US009269884B2

(12) United States Patent
Nakamura et al.

(10) Patent No.: US 9,269,884 B2
(45) Date of Patent: Feb. 23, 2016

(54) ULTRASONIC TRANSDUCER, ULTRASONIC PROBE, AND ULTRASONIC EXAMINATION DEVICE

(71) Applicant: SEIKO EPSON CORPORATION, Tokyo (JP)

(72) Inventors: Tomoaki Nakamura, Nagano (JP); Hironori Suzuki, Nagano (JP); Jiro Tsuruno, Nagano (JP)

(73) Assignee: Seiko Epson Corporation, Tokyo (JP)

( * ) Notice: Subject to any disclaimer, the term of this patent is extended or adjusted under 35 U.S.C. 154(b) by 348 days.

(21) Appl. No.: 13/896,700

(22) Filed: May 17, 2013

(65) Prior Publication Data

US 2013/0308425 A1 Nov. 21, 2013

(30) Foreign Application Priority Data

May 21, 2012 (JP) ................................. 2012-115320

(51) Int. Cl.
*B06B 1/06* (2006.01)
*H01L 41/08* (2006.01)
*G01S 15/02* (2006.01)

(52) U.S. Cl.
CPC .......... *H01L 41/0825* (2013.01); *B06B 1/0644* (2013.01); *G01S 15/02* (2013.01)

(58) Field of Classification Search
CPC . H01L 41/0825; H01L 41/092; H01L 41/098; G01S 15/02

USPC ......................................................... 367/140
See application file for complete search history.

(56) References Cited

U.S. PATENT DOCUMENTS

| | | | |
|---|---|---|---|
| 3,943,128 A * | 3/1976 | DeMarinis et al. | ........... 540/229 |
| 7,218,744 B2 | 5/2007 | Kobayashi | |
| 7,559,128 B2 * | 7/2009 | Kitagawa et al. | ............ 29/25.35 |
| 2006/0004290 A1 * | 1/2006 | Smith et al. | .................... 600/459 |
| 2011/0319766 A1 | 12/2011 | Tsuruno | |

FOREIGN PATENT DOCUMENTS

| | | |
|---|---|---|
| JP | 62-127195 U | 8/1987 |
| JP | 63-036126 A | 2/1988 |
| JP | 63-260298 A | 10/1988 |
| JP | 09-079930 A | 3/1997 |
| JP | 11-027798 A | 1/1999 |
| JP | 2000-23296 A | 1/2000 |
| JP | 2004-147286 A | 5/2004 |
| JP | 2006-165923 A | 6/2006 |
| JP | 2012-005690 A | 1/2012 |

\* cited by examiner

*Primary Examiner* — Mark Hellner
(74) *Attorney, Agent, or Firm* — Global IP Counselors, LLP (57) ABSTRACT

An ultrasonic transducer includes a substrate, a supporting film, and a piezoelectric element. The substrate includes an opening. The supporting film is configured on the substrate to cover the opening. The piezoelectric element is configured at a part of the supporting film. The part overlaps with the opening in a planar view in a thickness direction of the substrate. A thickness of the part of at a center of gravity in the planar view is smaller than a thickness of an outer edge portion of the part. The outer edge portion is closer to the substrate than the center to the substrate.

10 Claims, 8 Drawing Sheets

ULTRASONIC TRANSDUCER, ULTRASONIC PROBE, AND ULTRASONIC EXAMINATION DEVICE

CROSS-REFERENCE TO RELATED APPLICATIONS

This application claims priority to Japanese Patent Application No. 2012-115320 filed on May 21, 2012. The entire disclosure of Japanese Patent Application No. 2012-115320 is hereby incorporated herein by reference.

BACKGROUND

1. Technical Field

The present invention relates to an ultrasonic transducer, an ultrasonic probe, and an ultrasonic examination device.

2. Background Technology

An ultrasonic transducer in which a plurality of ultrasonic elements are arranged in a matrix pattern has been known. This ultrasonic transducer includes a substrate that has a plurality of openings, a supporting film that is provided on the substrate so as to cover each of the openings, and a piezoelectric element that is provided on a part of the supporting film corresponding to each of the openings. A diaphragm is constructed by the part of the supporting film corresponding to the opening which is a part coinciding with the opening of the supporting film in a planar view. The ultrasonic element is constructed by the diaphragm and the piezoelectric element provided on the diaphragm. The thickness of the supporting film of the ultrasonic transducer, that is, the thickness of the part of the supporting film corresponding to the opening which coincides with the opening of the supporting film in a planar view is set to be uniform (for example, see Patent Document 1). In the ultrasonic transducer, the diaphragm is greatly deflected when ultrasonic waves are transmitted, and the diaphragm is slightly deflected when ultrasonic waves are received.

The well-known ultrasonic transducer, however, has a problem that the diaphragm is greatly deflected especially when ultrasonic waves are transmitted, which causes the stress to concentrate in the vicinity of an outer edge portion of the diaphragm and causes damage such as cracking or chipping. On the other hand, if the thickness of the diaphragm is increased to improve the strength of the diaphragm, the diaphragm will become hard to deflect. Then, especially when ultrasonic waves are received with the ultrasonic element, the deflection amount of the diaphragm will become smaller, which makes the stress generated in the piezoelectric element very small. Consequently, the level of a reception signal output from the piezoelectric element will be deteriorated. In other words, the characteristics of transmission and reception of ultrasonic waves, in particular, the sensitivity in reception will be deteriorated.

Japanese Laid-open Patent Publication No. 2000-23296 (Patent Document 1) is an example of the related art.

SUMMARY

Problems to be Solved by the Invention

The advantage of the invention is to provide an ultrasonic transducer, an ultrasonic probe, and an ultrasonic examination device which have good characteristics of transmission and reception of ultrasonic waves, and can prevent the part of the supporting film corresponding to the opening from being damaged.

Means Used to Solve the Above-Mentioned Problems

This advantage is achieved by the invention described below. According to one aspect of the invention, an ultrasonic transducer includes a substrate, a supporting film, and a piezoelectric element. The substrate includes an opening. The supporting film is configured on the substrate to cover the opening. The piezoelectric element is configured at a part (an opening-overlapping part) of the supporting film. The part overlaps with the opening in a planar view in a thickness direction of the substrate. A thickness of the part at a center of gravity in the planar view is smaller than a thickness of an outer edge portion of the part. The outer edge portion is closer to the substrate than the center to the substrate.

According to another aspect of the invention, an ultrasonic transducer includes a substrate, a support film, and a piezoelectric element. The substrate includes an opening. The supporting film is configured on the substrate to cover the opening. The piezoelectric element is configured at a part of the supporting film. The part overlaps with the opening in a planar view in a thickness direction of the substrate. A surface of the part on an opening side having a curved concave surface.

BRIEF DESCRIPTION OF THE DRAWINGS

Referring now to the attached drawings which form a part of this original disclosure.

DETAILED DESCRIPTION OF EXEMPLARY EMBODIMENTS

Hereinafter, the ultrasonic transducer, the ultrasonic probe, and the ultrasonic examination device of the invention will be explained in detail based on a preferred embodiment shown in the attached drawings.

Embodiment of Ultrasonic Transducer and Ultrasonic Probe

Figure 1:
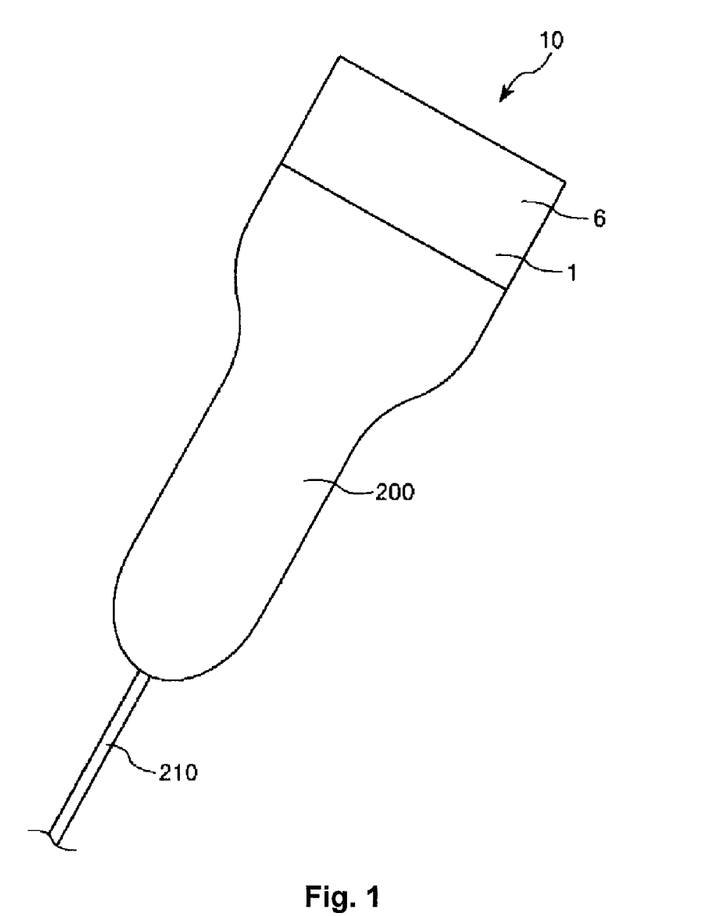
FIG. 1 is a perspective view showing an embodiment of an ultrasonic probe according to the invention.
Figure 2:
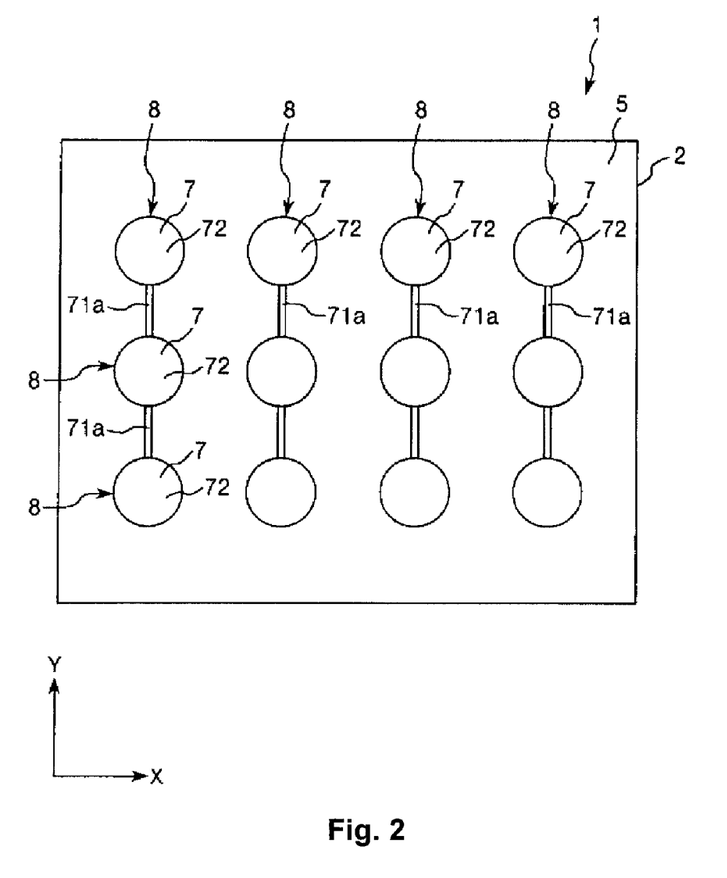
FIG. 2 is a plan view showing an ultrasonic transducer of the ultrasonic probe shown in FIG. 1.
Figure 3:
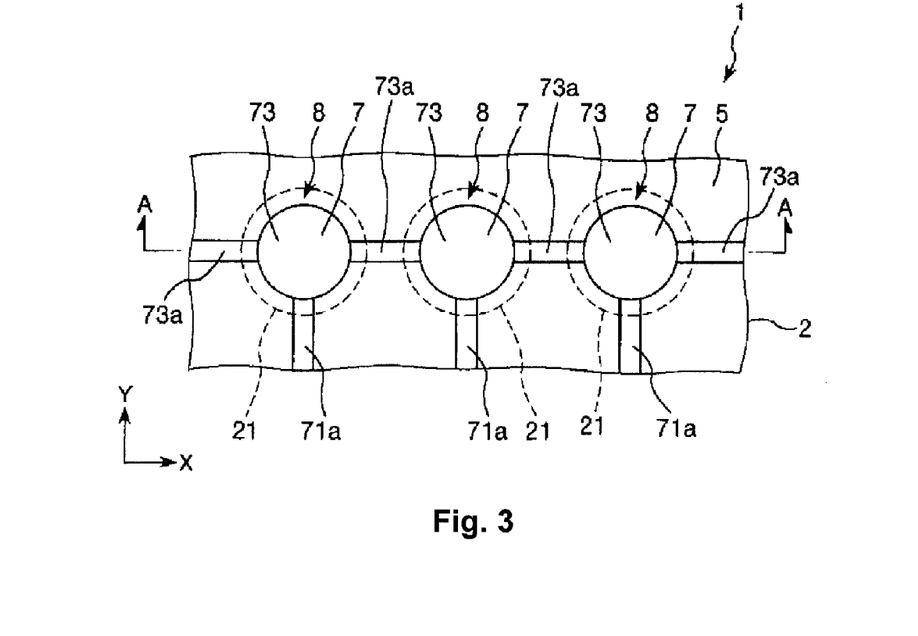
FIG. 3 is a plan view enlarging a part of the ultrasonic transducer shown in FIG. 2.
Figure 4:
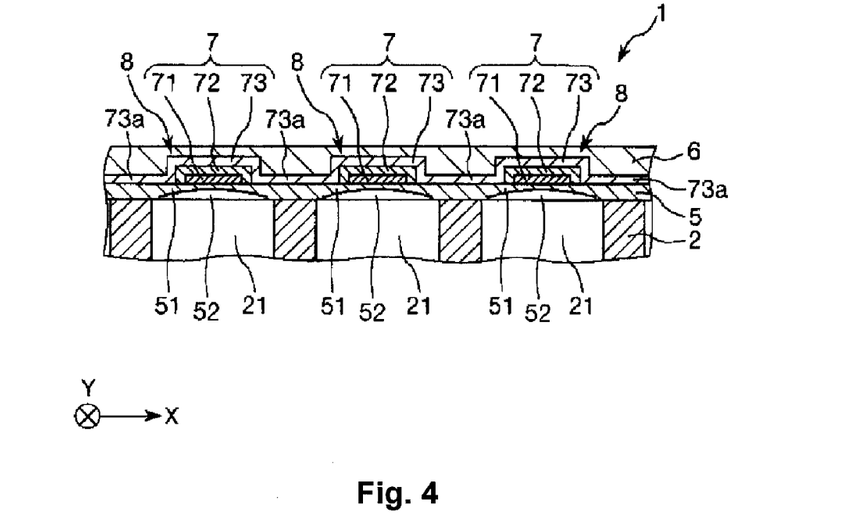
FIG. 4 is a sectional view along line A-A of FIG. 3.
Figure 5:
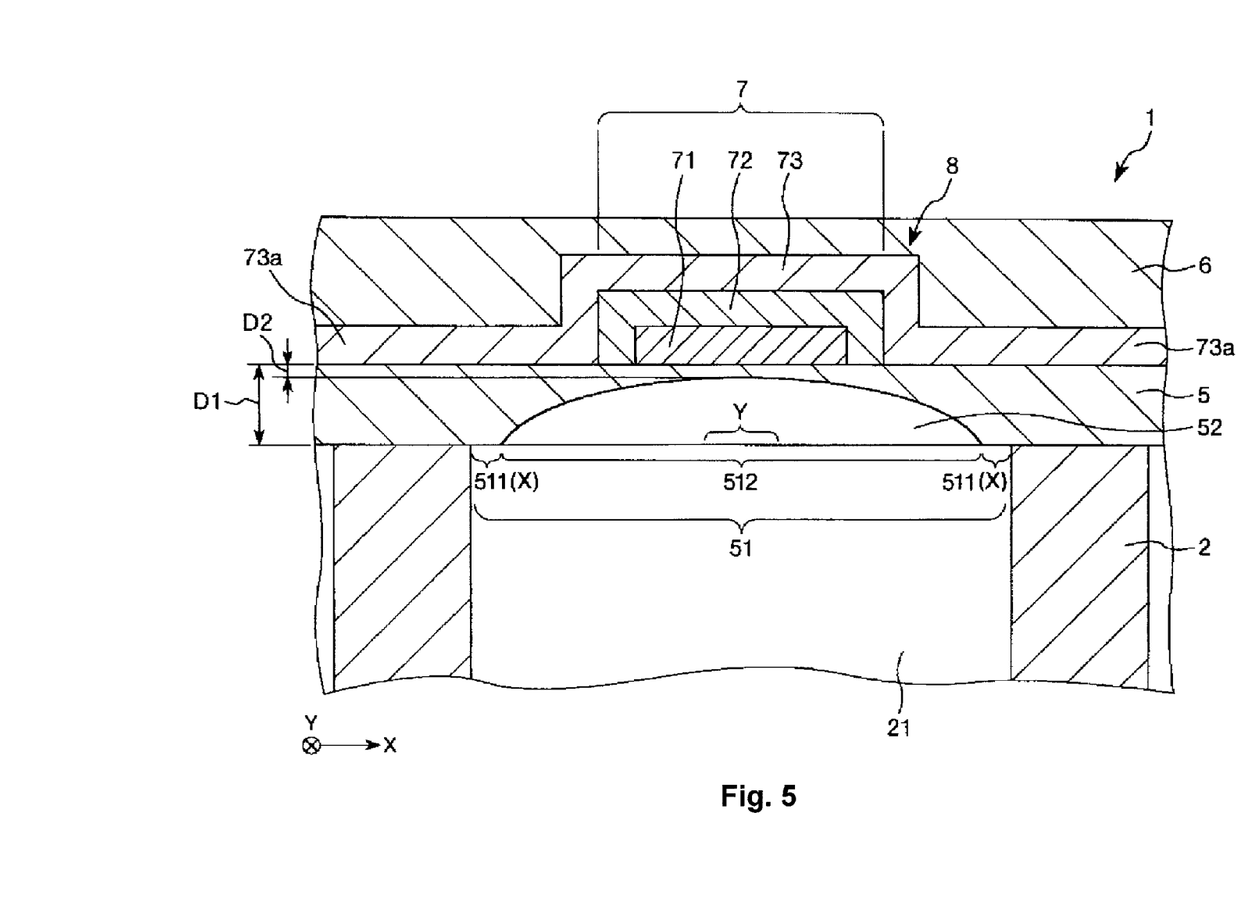
FIG. 5 is a sectional view enlarging a part of the ultrasonic transducer shown in FIG. 4.
Figure 6A:
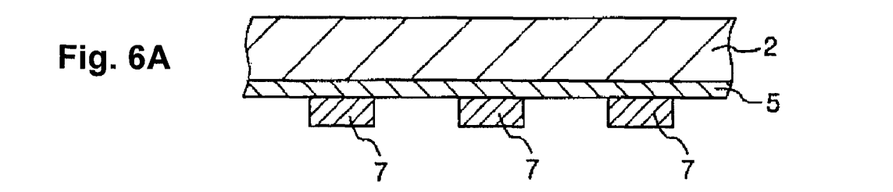
FIGS. 6A-6D are sectional views explaining a method for manufacturing the ultrasonic transducer of the ultrasonic probe shown in FIG. 1.
Figure 7A:
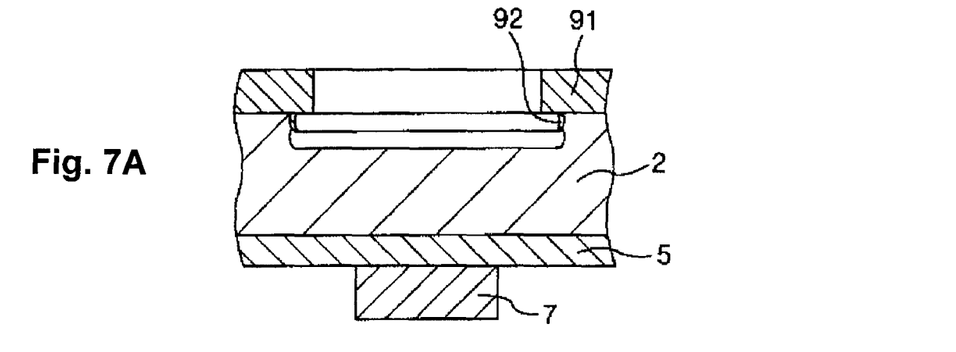
FIGS. 7A-7C are sectional views explaining a method for manufacturing the ultrasonic transducer of the ultrasonic probe shown in FIG. 1.
Figure 7B:
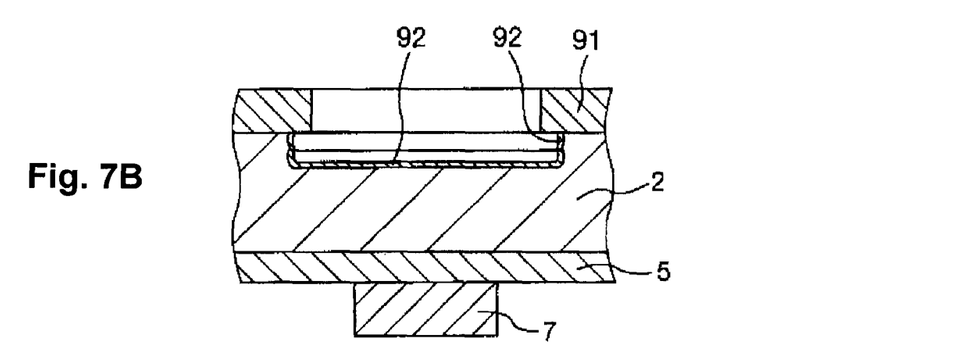
Figure 7C:
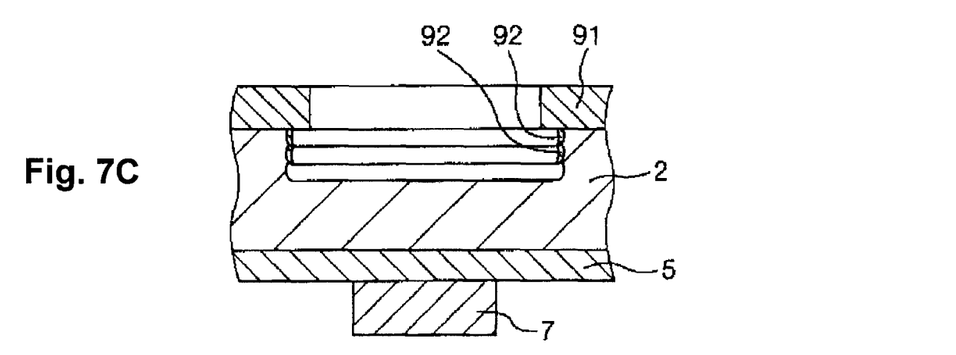
Figure 8:
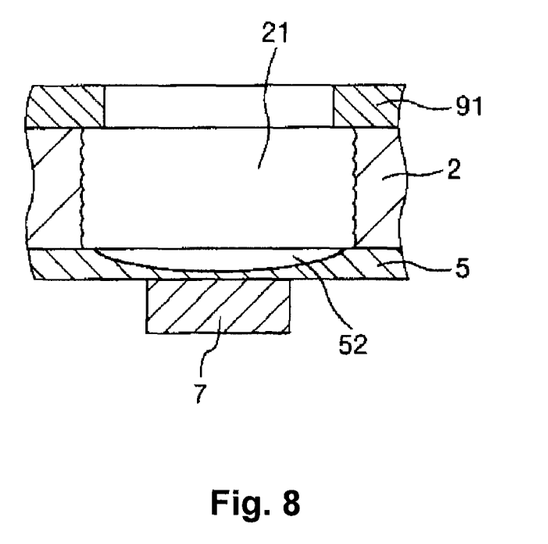
FIG. 8 is a sectional view explaining a method for manufacturing the ultrasonic transducer of the ultrasonic probe shown in FIG. 1.

FIG. 1 is a perspective view showing an embodiment of an ultrasonic probe according to the invention. FIG. 2 is a plan view showing an ultrasonic transducer of the ultrasonic probe shown in FIG. 1. FIG. 3 is a plan view enlarging a part of the ultrasonic transducer shown in FIG. 2. FIG. 4 is a sectional view along line A-A of FIG. 3. FIG. 5 is a sectional view enlarging a part of the ultrasonic transducer shown in FIG. 4. FIG. 6-FIG. 8 are sectional views explaining a method for manufacturing the ultrasonic transducer of the ultrasonic probe shown in FIG. 1. Hereinafter, explanations will be made by describing the upper side in FIG. 3-FIG. 7 as "upper", the lower side as "lower", the right side as "right", and the left side as "left".

In FIG. 2, illustrations of parts and the like of an acoustic matching section, an upper electrode, a lower electrode, a conducting wire for an upper electrode, and a conducting wire for a lower electrode are omitted, and the ultrasonic transducer is schematically illustrated. In FIG. 3, an illustration of the acoustic matching section is omitted. Further, in FIG. 6-FIG. 8, a piezoelectric element is schematically illustrated. Also, as shown in each drawing, an X axis and a Y axis orthogonal to each other are assumed. An X axis direction corresponds to an azimuth direction, and a Y axis direction corresponds to a slice direction.

As shown in FIG. 1, an ultrasonic probe 10 has a case 200, and an ultrasonic transducer 1 that is accommodated in the case 200. The ultrasonic transducer 1 is disposed in a tip end portion of the case 200. The ultrasonic probe 10 can be used as an ultrasonic probe for various kinds of ultrasonic examination devices such as an ultrasonic examination device 100 described below. In the present embodiment, a surface of the ultrasonic transducer 1, that is, a surface of an acoustic matching section 6 described below is exposed outside. The acoustic matching section 6 serves as a protective layer of the ultrasonic probe 10 and the ultrasonic transducer 1. Although the constituent material of the acoustic matching section 6 is not limited to a specific one, a material that is substantially similar to a living body with respect to the acoustic impedance, such as silicone rubber, is used. Here, it can be configured such that the surface of the acoustic matching section 6 is not exposed outside.

In conducting a test, the ultrasonic probe 10 is used by applying the surface of the acoustic matching section 6 to a living body as a test target. In such a case, when ultrasonic waves are sent out from the ultrasonic transducer 1 toward the acoustic matching section 6, the ultrasonic waves pass through the acoustic matching section 6 and propagate through the living body. Then, the ultrasonic waves reflected on a predetermined part inside the living body pass through the acoustic matching section 6 and are input to the ultrasonic transducer 1. Also, the ultrasonic probe 10 is electrically connected with a device main body 300 (see FIG. 9), described below, of the ultrasonic examination device 100 through a cable 210.

As shown in FIG. 2-FIG. 5, the ultrasonic transducer 1 has a substrate 2, a plurality of (twelve in the configuration shown in the drawing) ultrasonic elements (ultrasonic vibrators) 8 that are provided on the substrate 2 so as to transmit and receive ultrasonic waves, and the acoustic matching section 6 that is provided on the substrate 2 on the side of the ultrasonic elements 8 so as to cover each of the ultrasonic elements 8. Although the shape of the substrate 2 is not limited to a specific one, it forms a quadrangle in a planar view in the configuration shown in the drawing. Also, as another shape of the substrate 2 in a planar view, another polygon such as a pentagon or a hexagon, a circle, or an ellipse can be listed, for example. Although the constituent material of the substrate 2 is not limited to a specific one, a material for forming a semiconductor such as silicon (Si) is used, for example. Consequently, it can be processed easily by etching or the like.

The ultrasonic element 8 is constructed of a diaphragm 51 and a piezoelectric body (piezoelectric element) 7, and each of the ultrasonic elements 8 is arranged on the substrate 2 in a matrix pattern. In other words, the plurality of (four in the configuration shown in the drawing) ultrasonic elements 8 are arranged in parallel along the X axis direction, and the plurality of (three in the configuration shown in the drawing) ultrasonic elements 8 are arranged in parallel along the Y axis direction. Although the shape of the piezoelectric body 7 is not limited to a specific one, it forms a circle in a planar view in the configuration shown in the drawing. Also, as another shape of the piezoelectric body 7 in a planar view, a quadrangle (square, rectangle), a polygon such as a pentagon or a hexagon, or an ellipse can be listed, for example. Incidentally, the piezoelectric body 7 and the wiring thereof will be described below.

An opening 21 for forming the diaphragm 51 of the ultrasonic element 8 is formed in a part of the substrate 2 corresponding to each of the ultrasonic elements 8. Although the shape of the opening 21 is not limited to a specific one, it forms a circle in a planar view in the configuration shown in the drawing. Also, as another shape of the opening 21 in a planar view, a quadrangle (square, rectangle), a polygon such as a pentagon or a hexagon, or an ellipse can be listed, for example.

A supporting film 5 is formed on the substrate 2, and each of the openings 21 is covered with the supporting film 5. The diaphragm 51 is constructed by a part of the supporting film 5 corresponding to the opening which is a part (region) covering the opening 21, that is, a part coinciding with (part overlapping with) the opening 21 of the supporting film 5 in a planar view. The piezoelectric body 7 is provided on the diaphragm 51.

Although the constituent material of the supporting film 5 is not limited to a specific one, the supporting film 5 is constructed by a layered body (two-layer structure) of an $SiO_2$ film and a $ZrO_2$ layer, or an $SiO_2$ film, for example. In a case where the substrate 2 is an Si substrate, the $SiO_2$ layer can be formed by conducting a thermal oxidation treatment to the surface of the substrate 2. The $ZrO_2$ layer can be formed on the $SiO_2$ layer, for example, by a technique such as sputtering. Here, the $ZrO_2$ layer is a layer for preventing Pb that constitutes PZT from diffusing into the $SiO_2$ layer when PZT is used as a piezoelectric film 72 of the piezoelectric body 7, for example. The piezoelectric film 72 of the piezoelectric body 7 will be described below. The $ZrO_2$ layer also has an effect such as an effect of improving deflection efficiency with respect to deformation of the piezoelectric film 72.

As shown in FIG. 5, the piezoelectric body 7 has a lower electrode 71 formed on the diaphragm 51 (the supporting film 5), the piezoelectric film 72 formed on the lower electrode 71, and an upper electrode 73 formed on the piezoelectric film 72. Also, a conducting wire for a lower electrode 71a is connected with the lower electrode 71, and the conducting wire for a lower electrode 71a extends along the Y axis direction on the supporting film 5 as shown in FIG. 3, for example. The conducting wire for a lower electrode 71a serves as a common conducting wire of each ultrasonic element 8 arranged in the Y axis direction. More specifically, as shown in FIG. 3 and FIG. 4, the conducting wire for a lower electrode 71a is connected with the lower electrodes 71 of two adjacent ultrasonic elements 8 arranged in the Y axis direction. With this configuration, the assembly of the ultrasonic elements 8 arranged in the Y axis direction can be driven independently.

A conducting wire for an upper electrode 73a is connected with the upper electrode 73, and the conducting wire for an upper electrode 73a extends along the X axis direction on the supporting film 5 as shown in FIG. 3, for example. The conducting wire for an upper electrode 73a serves as a common conducting wire of each ultrasonic element 8 arranged in the X axis direction. More specifically, as shown in FIG. 3, the conducting wire for an upper electrode 73a is connected with the upper electrodes 73 of two adjacent ultrasonic elements 8 arranged in the X axis direction, and is connected to the GND, for example, at the end portion thereof. In this manner, the upper electrode 73 of each ultrasonic element 8 is earthed. Alternatively, contrary to the above, the conducting wire for a lower electrode 71a can be connected to the GND.

The constituent materials of the lower electrode 71, the upper electrode 73, the conducting wire for a lower electrode 71a, and the conducting wire for an upper electrode 73a are not limited to specific ones as long as they have conductive properties, respectively. For example, various kinds of metal materials can be used. Also, the lower electrode 71, the upper electrode 73, the conducting wire for a lower electrode 71a, and the conducting wire for an upper electrode 73a can be single layers, respectively, or can be layered bodies in which a plurality of layers are laminated, respectively. As specific examples, for example, a Ti/Ir/Pt/Ti layered film can be used as the lower electrode 71 and the conducting wire for a lower electrode 71a, respectively, and an Ir film can be used as the upper electrode 73 and the conducting wire for an upper electrode 73a, respectively.

The piezoelectric film 72 is made by forming PZT (lead zirconate titanate) into a film shape, for example. In the present embodiment, PZT is used as the piezoelectric film 72. However, any material can be used as long as it is a material that can contract (expand or contract) in an in-plane direction by applying a voltage thereto. For example, lead titanate ($PbTiO_3$), lead zirconate ($PbZrO_3$), lead lanthanum titanate (($Pb$, $La$) $TiO_3$), or the like can be used as well as PZT.

In the ultrasonic element 8, for example, when a voltage is applied between the lower electrode 71 and the upper electrode 73 by the device main body 300 (see FIG. 9) through the cable 210, the piezoelectric film 72 expands or contracts in the in-plane direction. In this instance, a surface of the piezoelectric film 72 is attached to the supporting film 5 through the lower electrode 71, and the upper electrode 73 is formed on the other surface thereof. Here, since any other layer is not formed on the upper electrode 73, the supporting film 5 side of the piezoelectric film 72 does not easily expand or contract, while the upper electrode 73 side of the piezoelectric film 72 easily expands or contracts. Therefore, when a voltage is applied to the piezoelectric film 72, deflection that causes projection occurs on the opening 21 side, which results in deflection of the first diaphragm 51. Consequently, when an alternating voltage is applied to the piezoelectric film 72, the diaphragm 51 vibrates with respect to the film thickness direction, and this vibration of the diaphragm 51 transmits (sends) ultrasonic waves. In transmission of such ultrasonic waves, an alternating voltage, whose frequency is equal to the resonance frequency of the ultrasonic element 8, or is close to the resonance frequency and is smaller than the resonance frequency, is applied to the piezoelectric film 72, and the ultrasonic element 8 is resonantly driven. With this, the diaphragm 51 is greatly deflected, so that ultrasonic waves can be transmitted with high output.

In receiving ultrasonic waves with the ultrasonic element 8, when ultrasonic waves are input to the diaphragm 51, the diaphragm 51 vibrates with respect to the film thickness direction. In the ultrasonic element 8, this vibration of the diaphragm 51 causes a potential difference between the surface of the piezoelectric film 72 on the lower electrode 71 side and the surface of the piezoelectric film 72 on the upper electrode 73, and a reception signal (detection signal) (current) is output from the upper electrode 73 and the lower electrode 71 in response to the displacement amount of the piezoelectric film 72. This signal is transmitted to the device main body 300 (see FIG. 9) through the cable 210, and predetermined signal processing or the like is conducted based on the signal. Then, in the device main body 300, an ultrasonic image (electronic image) is formed and displayed. In the ultrasonic probe 10, planar waves of ultrasonic waves can be transmitted in a desired direction by delaying and differentiating the timing of transmission of ultrasonic waves from each ultrasonic element 8 arranged in parallel along the X axis direction.

As shown in FIG. 5, in the ultrasonic transducer 1, a thickness of the part of the supporting film corresponding to the opening which coincides with the opening 21 of the supporting film 5 in a planar view, that is, a thickness of a central portion of the diaphragm 51 is smaller than a thickness of an outer edge portion of the diaphragm 51. Here, the outer edge portion of the part of the supporting film corresponding to the opening is an annular region X having a predetermined width from an outer circumferential end of the part of the supporting film corresponding to the opening toward the inside of the part of the supporting film corresponding to the opening, that is, toward the center of gravity in a planar view. The central portion of the part of the supporting film corresponding to the opening is a region Y having a predetermined area that includes the position of the center of gravity of the part of the supporting film corresponding to the opening except the region X (outer edge portion).

In the present embodiment, the diaphragm 51 has a uniform thickness portion 511 whose thickness is uniform in the outer edge portion thereof. The uniform thickness portion 511 is provided along the circumference of the diaphragm 51. In other words, the uniform thickness portion 511 has an annular shape in a planar view. The diaphragm 51 also has a gradually increasing thickness portion 512 whose thickness gradually increases from the center of gravity (the central portion) of the diaphragm 51 toward the outer edge portion thereof. A concave portion 52 having a curved surface curved in a bowl shape (curved concave surface) is formed in a lower surface of the diaphragm 51. With this configuration, the strength of the outer edge portion of the diaphragm 51, that is, the strength of the uniform thickness portion 511 is increased, and the gradually increasing thickness portion 512 of the diaphragm 51, in particular, the central portion side of the gradually increasing thickness portion 512 becomes easy to deflect. Consequently, damage such as cracking or chipping of the diaphragm 51 can be prevented from occurring while having good characteristics of transmission and reception of ultrasonic waves.

More specifically, even if the diaphragm 51 is greatly deflected in transmission and reception of ultrasonic waves, especially, in transmission of ultrasonic waves due to the resonant drive of the ultrasonic element 8, damage such as cracking or chipping can be prevented from occurring in the vicinity of the outer edge portion of the diaphragm 51. Further, since the central portion of the diaphragm 51 becomes easy to deflect locally, the deflection amount of the piezoelectric body 7 can be increased in transmission and reception of ultrasonic waves, especially, in reception of ultrasonic waves in which the deflection amount of the diaphragm 51 is small. Consequently, large stress is generated in the piezoelectric body 7, and the level of a reception signal output from the piezoelectric body 7 can be improved. In other words, the sensitivity in reception of ultrasonic waves can be improved. Further, the piezoelectric body 7 is provided closer to the central portion compared to the uniform thickness portion 511 on the diaphragm 51. Consequently, the sensitivity in reception of ultrasonic waves can be improved more securely.

Here, the size of the diaphragm 51 (the supporting film 5) is not limited to a specific one, and is determined based on various conditions. However, when the thickness of the uniform thickness portion 511 (outer edge) of the diaphragm 51 is D1 and the thickness of the position of the center of gravity (center) of the diaphragm 51 in a planar view is D2, D2/D1 is preferably within the range of 0.1 to 0.9. With this configuration, damage such as cracking or chipping can be prevented from occurring in the vicinity of the outer edge portion of the diaphragm 51 more securely, and the sensitivity in reception of ultrasonic waves can be improved more securely.

Preferably, the thickness D1 of the uniform thickness portion 511 (outer edge) of the diaphragm 51 is within the range of 0.4 μm to 1.5 μm. With this configuration, damage such as cracking or chipping can be prevented from occurring in the vicinity of the outer edge portion of the diaphragm 51 more securely. Preferably, the thickness D2 of the position of the center of gravity of the diaphragm 51 is within the range of 0.15 μm to 1.35 μm. With this configuration, the sensitivity in reception of ultrasonic waves can be improved more securely.

Further, when the area of the uniform thickness portion 511 of the diaphragm 51 is S1 and the area of the gradually increasing thickness portion 512 is S2 in a planar view, S1/S2 is preferably within the range of 0.02 to 0.25. With this configuration, damage such as cracking or chipping can be prevented from occurring in the vicinity of the outer edge portion of the diaphragm 51 more securely, and the sensitivity in reception of ultrasonic waves can be improved more securely. In the present embodiment, the diaphragm 51 has the uniform thickness portion 511. However, the uniform thickness portion 511 can be omitted.

Next, explanations will be made on an example of a method for processing the substrate 2 and the supporting film 5 in a method for manufacturing the ultrasonic transducer 1, that is, a method for forming each opening 21 of the substrate 2 and each concave portion 52 of the supporting film 5 (the diaphragm 51). Here, as one example, a case where the substrate 2 is composed of Si and the supporting film 5 is composed of $SiO_2$ will be described. First, as shown in FIG. 6(a), a structure including the substrate 2 with unformed opening 21, the supporting film 5 with unformed concave portion 52 above the substrate 2, and the piezoelectric body 7 above the supporting film 5 is manufactured. As a method for manufacturing this structure, since a conventionally known method or the like can be used, the explanations thereof will be omitted.

Next, each opening 21 is formed in the substrate 2 and each concave portion 52 is formed in the supporting film 5 by conducting processing to parts of the substrate 2 and the supporting film 5 corresponding to the piezoelectric body 7, respectively, so as to form each diaphragm 51. Since a method for forming each opening 21 is similar and a method for forming each concave portion 52 is similar, a method for forming one of the openings 21 and a method for forming one of the concave portions 52 will be explained hereinafter as representatives.

Figure 6B:
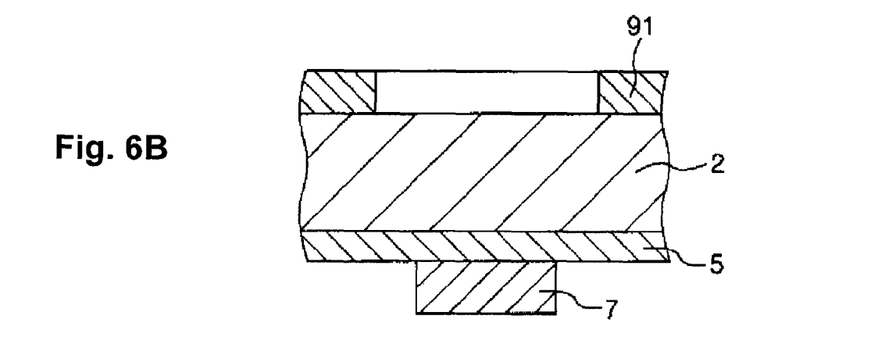
Figure 6C:
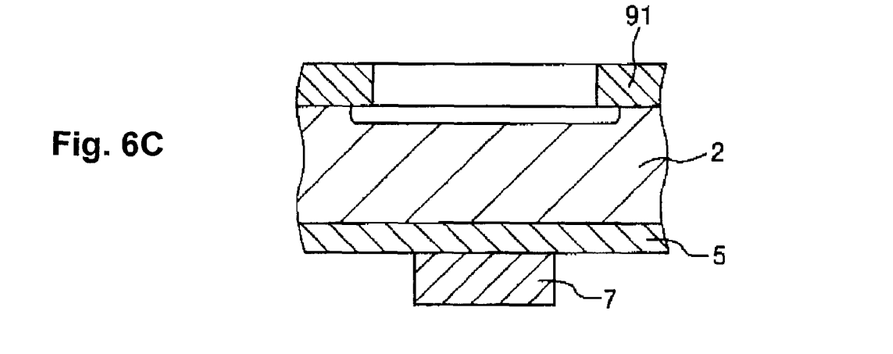
Figure 6D:
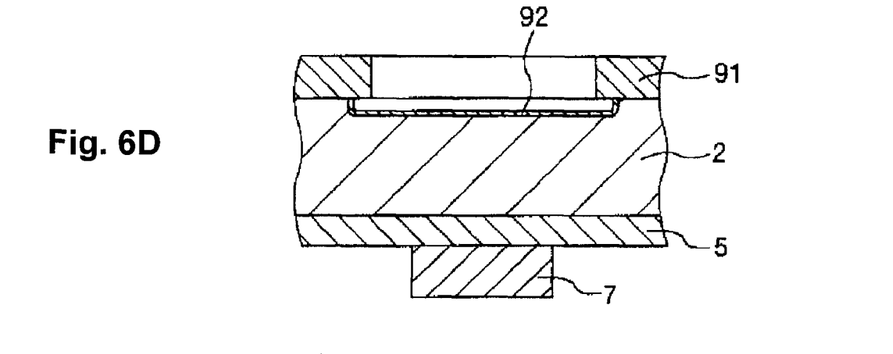

First, as shown in FIG. 6(b), a resist film 91 is formed on the upper surface of the substrate 2 except the part in which the opening 21 of the substrate 2 is formed. Next, as shown in FIGS. 6(c)-6(d), FIGS. 7(a)-7(c), and FIG. 8, the opening 21 is formed by the Bosch process (cycle etching) in which an etching process and formation of a protective film 92 are repeated alternately a plurality of times with respect to the substrate 2 using the resist film 91 as a mask. For this Bosch process, an inductively coupled (ICP) reactive ion etching apparatus is used. More specifically, inductively coupled reactive ion etching is conducted to the substrate 2 using an inductively coupled reactive ion etching apparatus in the etching process, and subsequently, the protective film 92 is formed in the substrate 2 using the inductively coupled reactive ion etching apparatus. In FIG. 6 and FIG. 7, a case where the etching process is conducted three times and the formation of the protective film 92 is conducted twice is illustrated. However, the numbers of times of the etching process and the formation of the protective film 92 are not limited to these numbers, respectively, and the actual numbers of times are larger than these numbers.

Here, in the etching process, mixed gas of $SF_6$ and $O_2$ is used as processing gas, for example. The flow rate of the processing gas in the etching process is not limited to a specific one, and is set as appropriate based on various conditions. However, for example, it is preferable to set within the range of 100 sccm to 1000 sccm, and it is more preferable to set within the range of 200 sccm to 700 sccm.

The processing time of the etching process is not limited to specific one, and is set as appropriate based on various conditions. However, for example, it is preferable to set within the range of 1 second to 20 seconds. The coil power of the inductively coupled plasma in the etching process is not limited to specific one, and is set as appropriate based on various conditions. However, for example, it is preferable to set within the range of 300 W to 3000 W.

Also, in forming the protective film 92, mixed gas of $C_4F_8$ and $O_2$ is used as processing gas, for example. The flow rate of the processing gas in forming the protective film 92 is not limited to a specific one, and is set as appropriate based on various conditions. However, for example, it is preferable to set within the range of 50 sccm to 600 sccm.

The time for forming the protective film 92 is not limited to specific one, and is set as appropriate based on various conditions. However, for example, it is preferable to set within the range of 0.5 second to 10 seconds. The coil power of the inductively coupled plasma in forming the protective film 92 is not limited to specific one, and is set as appropriate based on various conditions. However, for example, it is preferable to set within the range of 100 W to 2500 W. Incidentally, by composing the substrate 2 of Si, the opening 21 can be formed so as to be perpendicular to the upper surface and the lower surface of the substrate 2.

Next, as shown in FIG. 8, the concave portion 52 is formed by the Bosch process in which an etching process and formation of the protective film 92 are repeated alternately a plurality of times with respect to the supporting film 5 using the resist film 91 as a mask. For this Bosch process, an inductively coupled (ICP) reactive ion etching apparatus is used. More specifically, inductively coupled reactive ion etching is conducted to the supporting film 5 using an inductively coupled reactive ion etching apparatus in the etching process, and subsequently, a protective film which is not shown in the drawing is formed in the supporting film 5 using the inductively coupled reactive ion etching apparatus.

Here, in the etching process, mixed gas of $SF_6$ and $O_2$ is used as processing gas, for example. The flow rate of the processing gas in the etching process is not limited to a specific one, and is set as appropriate based on various conditions. However, for example, it is preferable to set within the range of 100 sccm to 1000 sccm, and it is more preferable to set within the range of 200 sccm to 700 sccm.

The processing time of the etching process is not limited to specific one, and is set as appropriate based on various conditions. However, for example, it is preferable to set within the range of 1 second to 20 seconds. The coil power of the inductively coupled plasma in the etching process is not limited to specific one, and is set as appropriate based on various conditions. However, for example, it is preferable to set within the range of 300 W to 3000 W.

Also, in forming the above-described protective film, mixed gas of $C_4F_8$ and $O_2$ is used as processing gas, for example. The flow rate of the processing gas in forming the protective film is not limited to a specific one, and is set as appropriate based on various conditions. However, for example, it is preferable to set within the range of 50 sccm to 600 sccm.

The time for forming the protective film is not limited to specific one, and is set as appropriate based on various conditions. However, for example, it is preferable to set within the range of 0.5 second to 10 seconds. The coil power of the inductively coupled plasma in forming the protective film is not limited to specific one, and is set as appropriate based on various conditions. However, for example, it is preferable to set within the range of 100 W to 2500 W. Incidentally, by composing the supporting film 5 of $SiO_2$, the concave portion 52 having a curved surface curved in a bowl shape is formed.

Next, the resist film 91 is removed. As described above, the ultrasonic transducer 1 is manufactured. Incidentally, the shape of the concave portion 52 such as the degree of curving of the concave portion 52 can be set as appropriate by adjusting the selected ratio of $Si/SiO_2$ or the like. Further, formation or non-formation of the uniform thickness portion 511, and the size of the uniform thickness portion 511 and the like in a case of forming the uniform thickness portion 511 can be set as appropriate by adjusting the flow rate of the processing gas in the etching process, the processing time of the etching process, the coil power of the inductively coupled plasma in the etching process, the flow rate of the processing gas in forming the protective film, the time for forming the protective film, the coil power of the inductively coupled plasma in forming the protective film, or the like. The ultrasonic probe 10 described above can be applied to an ultrasonic examination device in a preferred manner.

Next, an example of the conditions of each process in a case where the uniform thickness portion 511 is formed in the supporting film 5, and an example of the conditions of each process in a case where the uniform thickness portion 511 is not formed in the supporting film 5 will be described. These conditions are ones in a case where the thickness of the substrate 2 is 200 μm, Si is used as the constituent material of the substrate 2, and $SiO_2$ is used as the constituent material of the supporting film 5, respectively.

(1) The Case where the Uniform Thickness Portion 511 is Formed in the Supporting Film 5

First, in the etching process to the substrate 2, mixed gas of $SF_6$ and $O_2$ is used as the processing gas, the flow rate of the processing gas is 450 sccm, and the coil power is 2500 W. Also, in forming the protective film 92 in the substrate 2, mixed gas of $C_4F_8$ and $O_2$ is used as the processing gas, the flow rate of the processing gas is 150 sccm, and the coil power is 1500 W. The processing time of the etching process is 10 seconds, and the time for forming the protective film 92 is 6 seconds. The etching process and the formation of the protective film 92 are conducted alternately for 36 minutes in total.

Next, in the etching process to the supporting film 5, mixed gas of $SF_6$ and $O_2$ is used as the processing gas, the flow rate of the processing gas is 450 sccm, and the coil power is 2500 W. Also, in forming the protective film 92 in the supporting film 5, mixed gas of $C_4F_8$ and $O_2$ is used as the processing gas, the flow rate of the processing gas is 150 sccm, and the coil power is 1500 W. The processing time of the etching process is 10 seconds, and the time for forming the protective film 92 is 6 seconds. The etching process and the formation of the protective film 92 are conducted alternately for 14 minutes 24 seconds in total. With that, the process is finished.

(2) The Case where the Uniform Thickness Portion 511 is not Formed in the Supporting Film 5

First, in the etching process to the substrate 2, mixed gas of $SF_6$ and $O_2$ is used as the processing gas, the flow rate of the processing gas is 450 sccm, and the coil power is 2500 W. Also, in forming the protective film 92 in the substrate 2, mixed gas of $C_4F_8$ and $O_2$ is used as the processing gas, the flow rate of the processing gas is 150 sccm, and the coil power is 1500 W. The processing time of the etching process is 10 seconds, and the time for forming the protective film 92 is 6 seconds. The etching process and the formation of the protective film 92 are conducted alternately for 36 minutes in total.

Next, in the etching process to the supporting film 5, mixed gas of $SF_6$ and $O_2$ is used as the processing gas, the flow rate of the processing gas is 450 sccm, and the coil power is 2000 W. Also, in forming the protective film 92 in the supporting film 5, mixed gas of $C_4F_8$ and $O_2$ is used as the processing gas, the flow rate of the processing gas is 150 sccm, and the coil power is 1500 W. The processing time of the etching process is 5 seconds, and the time for forming the protective film 92 is 3 seconds. The etching process and the formation of the protective film 92 are conducted alternately for 20 minutes in total. With that, the process is finished.

Embodiment of Ultrasonic Examination Device

Figure 9:
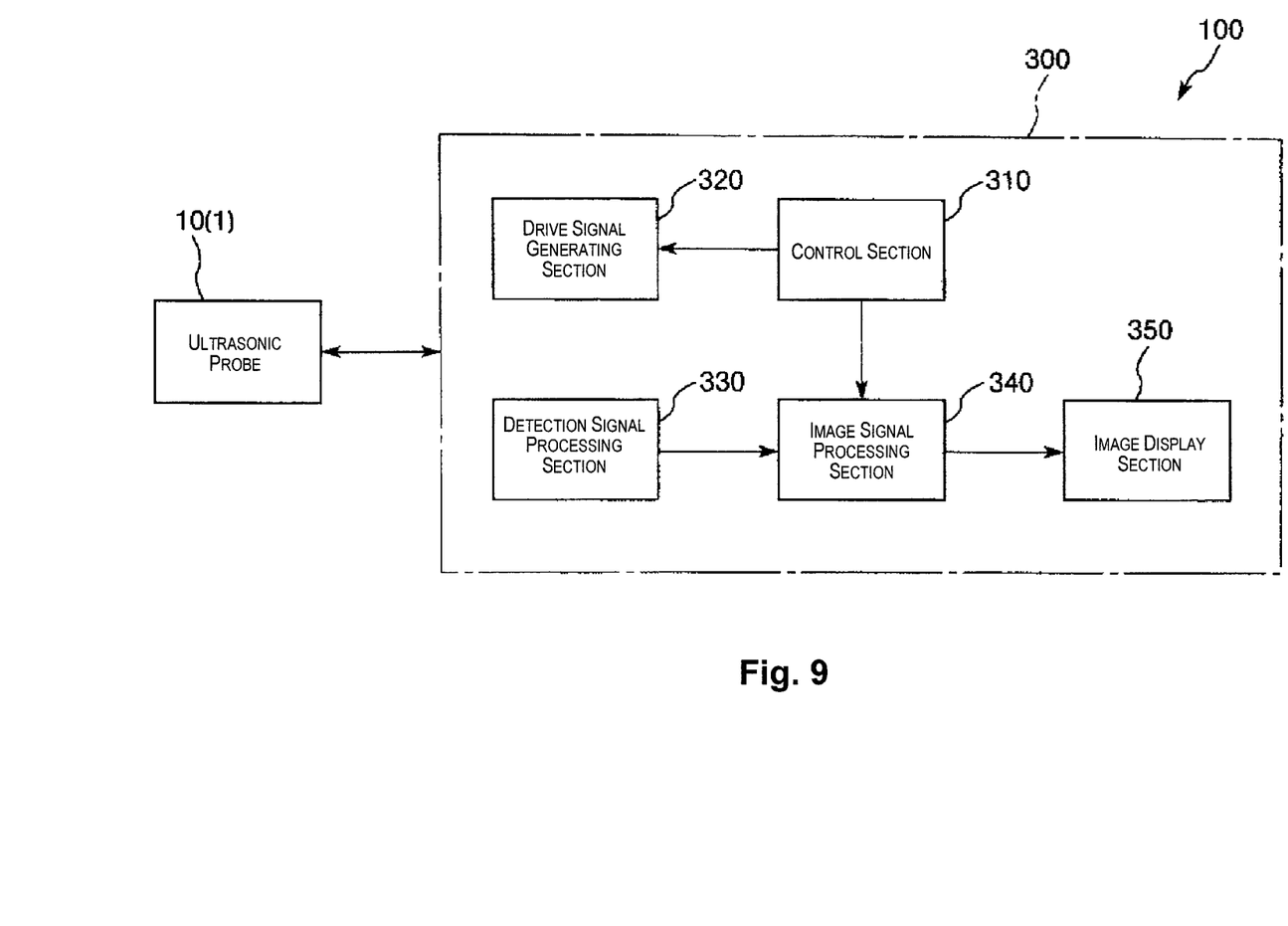
FIG. 9 is a block diagram showing an embodiment of an ultrasonic examination device according to the invention.

FIG. 9 is a block diagram showing the embodiment of the ultrasonic examination device according to the invention. As shown in FIG. 9, the diagnostic device 100 has the above-described ultrasonic probe 10, and the device main body 300 which is electrically connected with the ultrasonic probe 10 through the cable 210.

The device main body 300 has a control section (control means) 310, a drive signal generating section 320, a detection signal processing section 330, an image signal processing section 340, and an image display section (display means) 350. The signal processing section is constructed of the detection signal processing section 330 and the image signal processing section 340. The control section 310 is constructed of a microcomputer and the like, for example, and controls the entire device main body 300 such as the drive signal generating section 320 and the image signal processing section 340. The image display section 350 is constructed of a display device such as a CRT or an LCD, for example.

Next, the operation of the diagnostic device 100 will be explained. In conducting a test, the surface of the acoustic matching section 6 of the ultrasonic probe 10 is applied to a living body as a test target, and the diagnostic device 100 is activated. First, when the control section 310 outputs a transmission order to the drive signal generating section 320, the drive signal generating section 320 transmits a drive signal for driving each ultrasonic element 8 to the ultrasonic element 8 at a predetermined timing. In this manner, each of the ultrasonic elements 8 is driven at a predetermined timing. Then, ultrasonic waves are transmitted from the ultrasonic transducer 1 of the ultrasonic probe 10.

The transmitted ultrasonic waves propagate through a living body, and the ultrasonic waves reflected on a predetermined part of the living body are input to the ultrasonic transducer 1 of the ultrasonic probe 10. Then, a detection signal corresponding to the input ultrasonic waves are output from the ultrasonic transducer 1. The detection signal is transmitted to the detection signal processing section 330 of the device main body 300 through the cable 210. The detection signal undergoes predetermined signal processing in the detection signal processing section 330, and is converted into a digital signal by an A/D converter included in the detection signal processing section 330. The A/D converter is not shown in the drawing.

The digital signal output from the detection signal processing section 330 is input to the image signal processing section 340, and is sequentially stored in a primary storing section included in the image signal processing section 340 as areal data in synchronization with a frame timing signal. The primary storing section is not shown in the drawing. The image signal processing section 340 reconstructs two-dimensional or three-dimensional image data based on each areal data, and also conducts image processing such as interpolation, response emphasis processing, or tone processing to the image data. The image data, to which image processing has been conducted, is stored in a secondary storing section included in the image signal processing section 340. The secondary storing section is not shown in the drawing. The image data, to which image processing has been conducted, is then read out from the secondary storing section of the image signal processing section 340 and is input to the image display section 350. The image display section 350 displays an image based on the image data. A medical service worker such as a doctor conducts diagnosis or the like by observing an image displayed on the image display section 350.

The invention is not limited to the ultrasonic transducer, the ultrasonic probe, and the ultrasonic examination device of the invention explained in the above based on the embodiment shown in the drawing. The configuration of each section can be replaced with any configuration that has a similar function. Also, another optional element can be added to the invention. In the above-described embodiment, the number of the ultrasonic element, that is, the numbers of the parts of the piezoelectric element and the supporting film corresponding to the opening are plural, respectively. However, the invention is not limited to this, and they can be single.

GENERAL INTERPRETATION OF TERMS

In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts. Finally, terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing descriptions of the embodiments according to the present invention are provided for illustration only, and not for the purpose of limiting the invention as defined by the appended claims and their equivalents.

What is claimed is:

1. An ultrasonic transducer comprising:
a substrate including an interior surface defining an opening;
a supporting film being configured on the substrate to cover the opening, the supporting film including an opening-overlapping part overlapping with the opening in a plan view in a thickness direction of the substrate; and
a piezoelectric element being configured at the opening-overlapping part such that the opening-overlapping part is arranged between the opening and the piezoelectric element in the thickness direction,
the opening-overlapping part having a first portion with a center of gravity, a second portion arranged inward relative to the interior surface, and a third portion arranged between the first and second portions in the plan view, the first portion having a thickness in the thickness direction smaller than the second portion, the second portion being closer to the substrate than the first portion is to the substrate, the second portion having a uniform thickness in the thickness direction.

2. The ultrasonic transducer according to claim 1, wherein the third portion has the thickness of which gradually increases from the first portion toward the second portion.

3. An ultrasonic transducer comprising:
a substrate including an interior surface defining an opening;
a supporting film being configured on the substrate to cover the opening, the supporting film including an opening-overlapping part overlapping with the opening in a plan view in a thickness direction of the substrate; and
a piezoelectric element being configured at the opening-overlapping part such that the opening-overlapping part is arranged between the opening and the piezoelectric element in the thickness direction,
the opening-overlapping part having a curved concave surface on an opening side opening to the opening, and a uniform thickness portion that has a uniform thickness in the thickness direction and is disposed inward relative to the interior surface and disposed outward relative to the curved concave surface in the plan view.

4. The ultrasonic transducer according to claim 1, wherein the second portion is provided along an entire circumference of the supporting film.

5. The ultrasonic transducer according to claim 1, wherein the piezoelectric element is provided at an inside portion of the supporting film, which is further from the substrate than the second portion is from the substrate in the plan view.

6. The ultrasonic transducer according to claim 1, wherein the thickness of the second portion is D1,
the thickness of the first portion at the center of gravity is D2, and
D2/D1 is within the range of 0.1 to 0.9.

7. A probe comprising:
a case; and
the ultrasonic transducer according to claim 1 which is accommodated in the case.

8. An ultrasonic examination device comprising:
an ultrasonic probe which has a case, and the ultrasonic transducer according to claim 1 which is accommodated in the case; and
a device main body which has a signal processing section being configured to conduct a signal processing based on a signal transmitted from the ultrasonic probe.

9. The ultrasonic transducer according to claim 1, wherein the third portion has a continuously-curved concave surface.

10. The ultrasonic transducer according to claim 1, wherein
a plurality of piezoelectric elements including the piezoelectric element are arranged in an array pattern.

* * * * *